United States Patent [19]

Saito et al.

[11] Patent Number: 5,231,177
[45] Date of Patent: Jul. 27, 1993

[54] SODIUM N-ACETYLNEURAMINATE TRIHYDRATE

[75] Inventors: Kinichi Saito, Sayama; Hideo Mizu, Urawa; Naokazu Sugiyama, Hoya; Shikoh Minagawa, Yamagata; Motoaki Goto, Tokorozawa; Kenji Abiko, Kaminoyama, all of Japan

[73] Assignee: Mect Corporation, Tokyo, Japan

[21] Appl. No.: 488,860

[22] Filed: Mar. 5, 1990

[30] Foreign Application Priority Data

Mar. 8, 1989 [JP] Japan .................................. 1-55388

[51] Int. Cl.$^5$ ....................... C07H 5/06; C07H 13/02; A61K 31/70
[52] U.S. Cl. .................................. 536/53; 536/1.11; 536/127; 422/40
[58] Field of Search ................ 536/1.1, 53, 55.3, 127; 23/295 R; 422/40; 514/23

[56] References Cited

U.S. PATENT DOCUMENTS

| 4,758,660 | 7/1988 | Takeuchi et al. | 536/127 |
| 4,797,477 | 1/1989 | Yoshimura et al. | 536/53 |
| 4,914,195 | 4/1990 | Ogura et al. | 536/53 |
| 4,968,786 | 11/1990 | Ogawa et al. | 536/123 |
| 4,997,923 | 3/1991 | Izawa et al. | 536/127 |
| 5,003,061 | 3/1991 | Carobbi et al. | 536/127 |

FOREIGN PATENT DOCUMENTS

| 0039981 | 11/1981 | European Pat. Off. | 536/4.1 |
| 1-299294 | 12/1989 | Japan | 536/53 |

OTHER PUBLICATIONS

Flippen; Chemical Abstracts 79:119387c (1973).
Ogura et al; Chemistry Letters pp. 1003–1006; 1984 (6).
Sugiyama et al; Analytical Sciences 5(4):491–492 (Aug. 1989).
Chemical Abstracts, vol. 59, No. 6, Sep. 16, 1963, Columbus, Ohio, USA.
H. Rinderknecht et al. "Synthesis of N-acetylneuraminic acid" Column 6497b.
Chemical Abstracts, vol. 52, No. 3, Feb. 10, 1958, Columbus, Ohio, USA.
Yoshiharu Saito "Preparation of sialic acid or acetylneuraminic acid" Column 1923g.
Chemical Abstracts, vol. 51, No. 18, Sep. 25, 1957, Columbus, Ohio, USA.
Cornforth et al. "Synthesis of N-acetylneuraminic acid (lactaminic acid), O-sialic acid)" Column 13858f.

Primary Examiner—Johnnie R. Brown
Assistant Examiner—Nancy S. Carson
Attorney, Agent, or Firm—Oblon, Spivak, McClelland, Maier & Neustadt

[57] ABSTRACT

Sodium N-acetylneuraminate trihydrate herein provided is represented by the following formula:

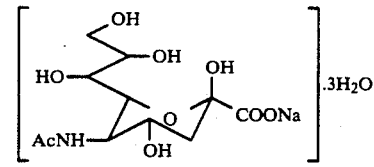

The sodium N-acetylneuraminate trihydrate can be prepared, for instance, according to a method which comprises the steps of: dissolving sodium N-acetylneuraminate in water or in a mixture of water and an organic solvent; allowing the resulting solution to stand; precipitating and separating the resulting crystals of sodium N-acetylneuraminate.trihydrate; and then drying the separated crystals. The sodium N-acetylneuraminate trihydrate has very low hygroscopicity and hence can be handled without any difficulty in the form of powder.

4 Claims, 1 Drawing Sheet

SODIUM N-ACETYLNEURAMINATE TRIHYDRATE

BACKGROUND OF THE INVENTION

1. Field of the Invention

The present invention relates to sodium N-acetylneuraminate.trihydrate. More specifically, the present invention pertains to sodium N-acetylneuraminate trihydrate which has low hygroscopicity and high storage stability as well as a method for preparing the same.

2. Description of the Prior Art

N-Acyl and O-acyl derivatives of polyhydroxy monoaminocarboxylic acid (neuraminic acid) are called sialic acids and are widely distributed throughout the living bodies of animals as constituents of mucopolysaccharides, glycoproteins and glycolipids.

The sialic acids are present at the ends of sugar chains of the glycoproteins and the glycolipids of animal cell membranes in large quantities, contribute to the occurrence of the negative charges on the cell surface, and play an important role in the specific recognizing-mechanism of the cell.

As already described above, the sialic acid acts as an acid because it has a carboxyl group. Thus, it can easily be converted into alkali metal salts or alkaline earth metal salts.

N-acetylneuraminic acid (hereafter referred to as "NANA" for simplicity) is a known compound and a typical example of a sialic acid. In addition, the present applicant already filed a patent application which claims an invention relating to an expectorant containing a compound represented by the following general formula as an effective component (Japanese Patent Publication for Opposition Purpose No. Sho 63-28411; now Japanese patent No. 1,478,542):

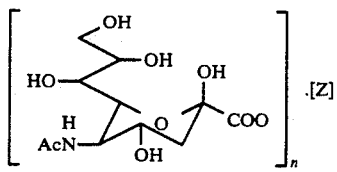

(wherein, if n=1, Z represents hydrogen, lithium, potassium or sodium, or an ammonium or organic ammonium group or, if n=2, Z represents calcium, barium or magnesium.)

However, N-acetylneuraminates (salts) are in general hygroscopic and it is difficult to handle them in powder form. Therefore, their preservation and storage are correspondingly very difficult.

SUMMARY OF THE INVENTION

Accordingly, an object of the present invention is to provide an N-acetylneuraminic acid derivative having low hygroscopicity and good handling properties.

Another object of the present invention is to provide a method for preparing such a derivative of NANA.

The inventors of this invention have conducted various studies to obtain salts of NANA which have low hygroscopicity and which are easily handled in powder form, have found that the foregoing disadvantages of the conventional salts of NANA can be effectively eliminated by converting the salts into their hydrate forms.

The foregoing objects of the present invention can effectively be achieved by providing novel sodium N-acetylneuraminate.trihydrate (hereunder also referred to as "NANA-Na.3H2O", if necessary) and in particular sodium N-acetylneuraminate.trihydrate which has low hygroscopicity and is hence easily handled in powder form (fine powder). More specifically, the present invention provides sodium N-acetylneuraminate.trihydrate which can be stored or preserved without using any conventionally known desiccants or the like, as well as a simple method for preparing NANA-Na.3-H2O.

BRIEF EXPLANATION OF THE DRAWING

The FIGURE is a diagram showing the stereostructural formula of the molecule: NANA-Na.3H2O obtained according to the X-ray crystallographic analysis, in which the serial number of each atom is also shown.

DETAILED DESCRIPTION OF THE PREFERRED EMBODIMENTS

Figure 1:
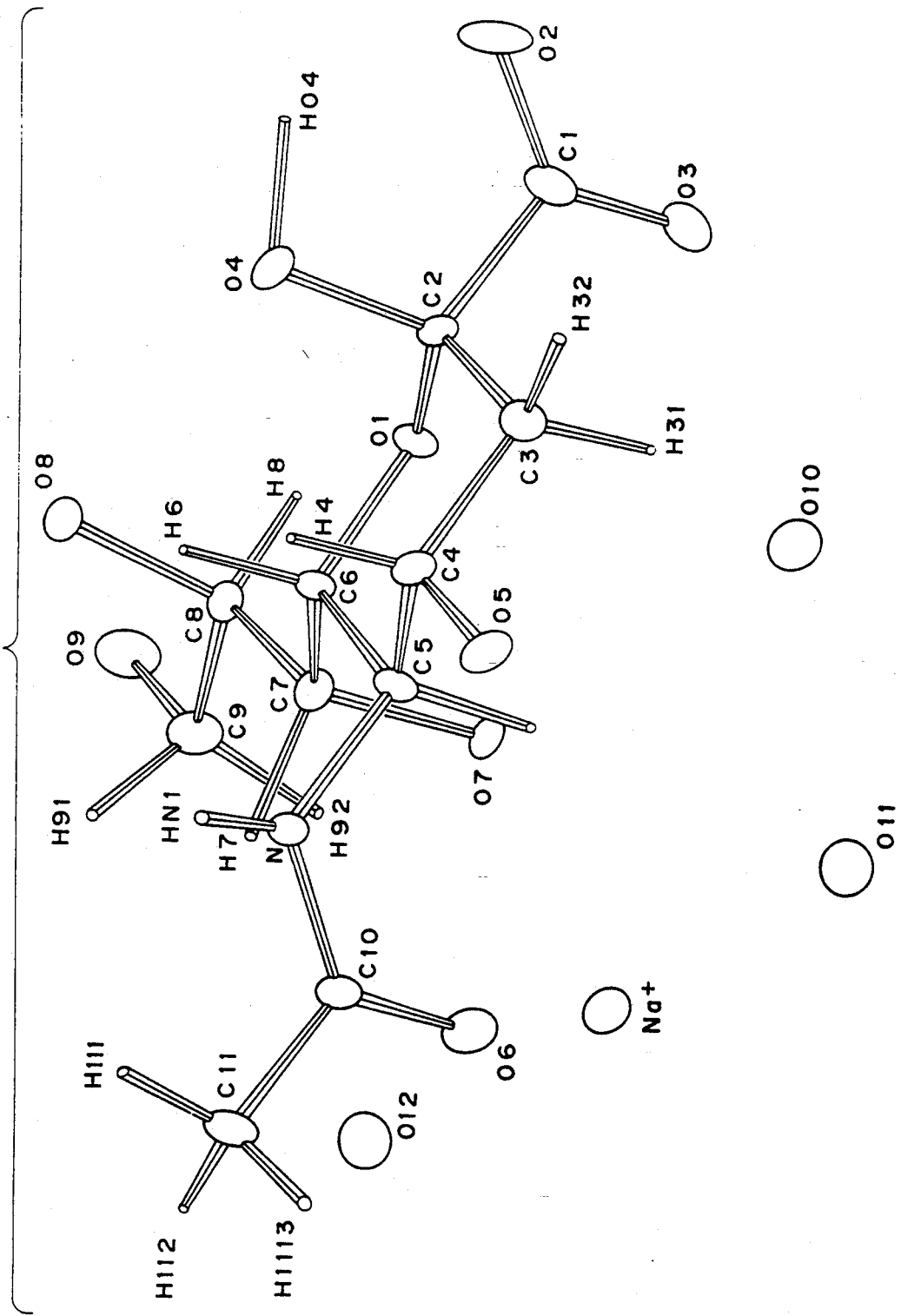

The sodium N-acetylneuraminate.trihydrate of the present invention will hereunder be described in more detail.

The NANA-Na.3H2O according to the present invention is represented by the following structural formula:

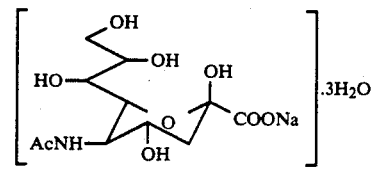

N-Acetylneuraminic anhydride is a known compound in itself. Its sodium salt can be obtained, for instance, by neutralizing the anhydride with an aqueous solution of a sodium compound such as sodium hydroxide or sodium carbonate and then separating the resulting sodium salt in an appropriate manner.

The NANA-Na thus obtained is sufficiently dried, then divided into fine powder and thus employed in the usual applications.

Powder of sodium N-acetylneuraminate conventionally prepared suffers from various drawbacks as explained above, but these drawbacks can effectively be eliminated if the salt is converted into its trihydrate form.

The sodium N-acetylneuraminate.trihydrate of the present invention can be prepared according to a variety of methods. For instance, it can be prepared by dissolving sodium N-acetylneuraminate in water or a mixture of water with an organic solvent in a desired rate with heating the mixture if necessary, then allowing the solution or the mixture to stand for 2 to 3 days at, for instance, room temperature and separating the resulting crystals in an appropriate manner such as precipitation by addition of a poor solvent followed by centrifugation, filtration or evaporation of solvents. The crystals are then dried under a reduced pressure.

Preferred examples of the organic solvent include water miscible, polar organic solvents such as ethanol, acetone, acetonitrile, tetrahydrofurane and dioxane. These organic solvents are, preferably, poor solvents for NANA-Na. Ethanol is most preferably employed in the present invention since it is easily eliminated from the resulting trihydrate and it is safe to the human body. The ratio (v/v) of water to an organic solvent and that of sodium N-acetylneuraminate to the mixed solvent are not critical in the present invention, but the mixed solvent preferably contains more than 50% and less than 80% of the organic solvent and the ratio of NANA-Na to the mixed solvent preferably ranges from about 2:5 to about 1:40 in order to obtain the desired trihydrate in a high yield. Likewise, the time for allowing the solution to stand and that for drying the resulting crystals are not critical in the invention.

The trihydrate according to the present invention can also be prepared by dissolving sodium N-acetylneuraminate in a small amount of water (the weight ratio, NANA-Na/water, is not more than about 1) and then drying the resulting aqueous solution with growing the trihydrate crystals.

Alternatively, the trihydrate can be prepared by storing sodium N-acetylneuraminate in a sealed container in which the relative humidity is maintained at a desired level. In order to achieve an industrially acceptable crystal growth rate, it is desirable that the relative humidity in the container range from 60 to 80%.

The method for preparing the NANA-Na.3H$_2$O according to the invention will be more specifically described below with reference to the following non-limiting Examples. The practical advantages of the invention will also be discussed in connection with the Comparative Example.

EXAMPLE 1

Various crystallization conditions as detailed in the following Table were performed to prepare the trihydrate of sodium N-acetylneuraminate according to the present invention. In other words, to A g of sodium N-acetylneuraminate was added to C ml of a B% ethanol.water mixed solvent, the mixture was heated at 60° to 70° C. to dissolve the sodium salt, allowed to stand for 2 to 3 days at room temperature and the resulting crystals were separated by filtration. Thereafter the crystals were washed with the same ethanol.water mixed solution stated above and dried for 24 hours under a reduced pressure to give the desired sodium N-acetylneuraminate.trihydrate in a yield of D% listed in the following Table.

| B | A (g) | C (ml) | D (%) |
|---|---|---|---|
| 50% Ethanol | 4.05 | 10.5 | 15.8 |
| 70% Ethanol | 0.5 | 4.1 | 61.5 |
| 70% Ethanol | 2.05 | 14.1 | 63.9 |
| 75% Ethanol | 2.03 | 29.2 | 54.7 |
| 80% Ethanol | 2.05 | 79 | 43.3 |
| 75% Ethanol | 10 | 200 | 57.6 |
| 65% Ethanol | 10 | 40 | 61.7 |
| 65% Ethanol | 10 | 50 | 52.7 |
| 80% Ethanol | 10 | 100 | 56.9 |
| 70% Ethanol | 10 | 200 | 48.3 |

The physical properties of the resulting product (NANA-Na.3H$_2$O) are as follows:

IR $\nu_{max}$ (KBr) cm$^{-1}$: 3325, 1666, 1620, 1551, 1113, 1043

Elemental Analysis (for C$_{11}$H$_{18}$NNaO$_9$.3H$_2$O): Found (%): C, 34.14; H, 6.26; N 3.62. Calc. (%): C, 34.29; H, 6.28; N, 3.64.

Melting Point (m.p.): 98°∼101° C.

Crystallographic Data: Molecular Formula: C$_{11}$H$_{24}$O$_{12}$NNa. Molecular Weight: 385.30. Lattice Constants: a 7.501(2) Å. b 7.501(2) Å. c 29.363(5) Å. Crystal System: tetragonal system. Space Group: P4$_1$. Volume of Unit Lattice: 1652.1 Å$^3$. Number of Molecules per Unit Lattice: 4. Density (calculated): 1.549 g·cm$^{-3}$. Density (found): 1.54 g·cm$^{-3}$. R=4.7%.

The stereostructural formula of the sodium N-acetylneuraminate.trihydrate molecule was also determined in terms of the X-ray crystallographic analysis and shown in FIG. 1. As is seen from the figure the isomeric carbons have the following stereo-configurations: C$_2$ is S; C$_4$ is S; C$_5$ is R; C$_6$ is R, and C$_8$ is R.

On the other hand, the following experiments were performed on NANA.Na anhydride for comparison.

REFERENCE EXAMPLE 1

Preparation of Sodium N-Acetylneuraminate 500 g of N-acetylneuraminate was dissolved in 5,000 ml of water, 5 g of active carbon was added thereto and 1617 ml of a 1N sodium hydroxide solution was added to the solution in a nitrogen gas stream to adjust pH to 7.8. The reaction solution was filtered through a 0.2 μm filter and the filtrate was lyophilized to give 535 g (constant amount) of sodium N-acetylneuraminate as colorless powder.

The physical properties of the resulting product are as follows:

IR $\nu_{max}$ (KBr) cm$^{-1}$: 3370, 1628, 1153, 1129, 1031.

Elemental Analysis (for C$_{11}$H$_{18}$NNaO$_9$): Found (%): C, 39.88; H, 5.48; N, 4.23. Calc. (%): C, 39.81; H, 5.77; N, 4.21.

Melting Point (decomposition point): The product causes foaming at 138° to 157° C. The product gets colored at 168° to 175° C. The foaming comes to an end at 181° to 187° C.

EXAMPLE 2

Evaluation of the Hygroscopicity of NANA-Na.3H$_2$O at Critical Relative Humidity (hereunder referred to as "CRH") (According to the Saturated Solution Method)

Specimen: NANA-Na.3H$_2$O

Agents

Chromium trioxide: Guaranteed reagent (available from WACO PURE CHEMICAL INDUSTRIES, LTD.)

Sodium bromide: Guaranteed reagent (available from WACO PURE CHEMICAL INDUSTRIES, LTD.)

Ammonium sulfate: Guaranteed reagent (available from WACO PURE CHEMICAL INDUSTRIES, LTD.)

Ammonium phosphate: Guaranteed reagent (available from WACO PURE CHEMICAL INDUSTRIES, LTD.)

Machinery and Tools

Balance: 2004 MP6E (available from ZARTRIUS CO., LTD.)

Incubator: IB-81 (available from YAMATO KAGAKU CO., LTD.)

Stirrer: PC-351 (available from IWAKI GLASS CO., LTD.)

Method of Operation

A saturated solution of a standard substance was allowed to stand in an environment having varying humidity for a predetermined time, the relative humidity at which the standard substance never showed any increase or decrease in its weight was calculated according to the interpolation technique and the value of the relative humidity was defined as the CRH of the substance.

This experiment was performed under the three conditions listed in the following Table.

|  | Condition (1) | Condition (2) | Condition (3) |
|---|---|---|---|
| Soln. Providing a Const. Humidity | a · b · c | a · b · c | b · c · d |
| Time for Allowing to Stand (hrs.) | 5 | 22 | 4.5 |

Solution a: A saturated solution of chromium trioxide
Solution b: A saturated solution of ammonium sulfate.
Solution c: A saturated solution of ammonium phosphate.
Solution d: A saturated solution of sodium bromide.

Results

The results thus obtained are summarized in the following Table.

| Condn. | Soln. | Humidity[*1] (%) [x] | Av. Change in Weight[*2] (%) [y] | Regression Line | CRH (%) |
|---|---|---|---|---|---|
| (1) | a | 39.2 | −5.48 | a = −10.16 | 87.3 |
| (1) | b | 80.1 | −1.33 | b = 0.12 | 87.3 |
| (1) | c | 92.9 | 1.03 | r = 0.991 | 87.3 |
| (2) | a | 39.2 | −24.31 | a = −44.3 | 87.6 |
| (2) | b | 80.1 | −4.75 | b = 0.51 | 87.6 |
| (2) | c | 92.9 | 3.37 | r = 0.998 | 87.6 |
| (3) | b | 80.1 | −0.84 | a = −4.52 | 85.8 |
| (3) | c | 92.9 | 0.71 | b = 0.053 | 85.8 |
| (3) | d | 58.5 | −1.24 | r = 0.889 | 85.8 |

[*1]The relative humidity (reported in the literature) of each solution for providing a constant humidity at 22.8° C.
[*2]Change in Weight (%) = (Variation in weight)/(weight of the saturated solution of each standard substance) × 100.

From the foregoing results, it can be elucidated that the CRH of NANA-Na.3H$_2$O at 22.8° C. is about 87%.

The same procedures were repeated with the comparative sample, NANA-Na, and the CRH thereof was found to be about 26%.

In general, it is desired that the humidity of the environment in which agents of this kind are handled be lower than the CRH by 20 to 30%.

Therefore, it can be concluded that a substance having a CRH value on the order of 87% no longer absorbs moisture in an environment maintained at room temperature and the normal conditions of relative humidity.

EXAMPLE 3

One gram of sodium N-acetylneuraminate was dissolved in 1 ml of water and then dried in a desiccator (desiccant=silica gel) for 2 days. As a result, sodium N-acetylneuraminate.trihydrate was obtained in an yield of 100%.

EXAMPLE 4

10 g of sodium N-acetylneuraminate was dissolved in 20 ml of water and then condensed under a reduced pressure. After the crystal growth thereof, an 80% aqueous ethanol solution was added to the solution to precipitate crystals and the crystals were filtered off. The resulting trihydrate crystals were washed with an 80% aqueous ethanol solution and then dried under a reduced pressure (yield=NANA-Na.trihydrate 82%).

EXAMPLE 5

One gram of sodium N-acetylneuraminate was stored in a reservor maintained at a constant humidity of 75% RH. 3 Kays thereafter, the crystallization of the trihydrate was completed (yield=NANA-Na.trihydrate 100%).

What is claimed is:

1. Sodium N-acetylneuraminate.trihydrate represented by the following formula:

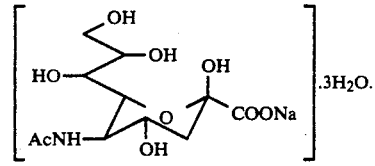

2. Sodium N-acetylneuraminate.trihydrate according to claim 1 having lattice constants a=7.501(2) Å, b=7.501(2) Å and C=29.363(5) Å in a tretragonal system of space group P4$_1$.

3. A sodium N-acetylneuraminate.trihydrate according to claim 1, wherein C$_2$ has an S configuration, C$_4$ has an S configuration, C$_5$ has an R configuration, C$_6$ has an R configuration, and C$_8$ has an R configuration.

4. The sodium N-acetylneuraminate.trihydrate of claim 1, wherein said sodium N-acetylneuraminate is in powder form.

* * * * *